(12) United States Patent
Riegel

(10) Patent No.: US 8,397,647 B1
(45) Date of Patent: Mar. 19, 2013

(54) MEDICAL DEVICE STAND AND SYSTEM

(75) Inventor: Mark Franklin Riegel, Fleetwood, PA (US)

(73) Assignee: Mark Franklin Riegel, Fleetwood, PA (US)

( * ) Notice: Subject to any disclaimer, the term of this patent is extended or adjusted under 35 U.S.C. 154(b) by 311 days.

(21) Appl. No.: 12/860,996

(22) Filed: Aug. 23, 2010

Related U.S. Application Data

(60) Provisional application No. 61/250,360, filed on Oct. 9, 2009.

(51) Int. Cl.
  *A47B 37/00* (2006.01)
(52) U.S. Cl. .......................... 108/24; 108/26
(58) Field of Classification Search ............ 108/24–26, 108/14, 147.19, 153.1, 147.21, 155, 157.2, 108/158.11; 312/229, 209, 330.1; 119/753; 5/606
See application file for complete search history.

(56) References Cited

U.S. PATENT DOCUMENTS

| | | | | |
|---|---|---|---|---|
| 1,437,670 A | * | 12/1922 | Mazoch | 108/147.21 |
| RE17,901 E | * | 12/1930 | Brogden | 66/1 R |
| 2,619,307 A | * | 11/1952 | Cramer | 248/680 |
| 3,000,683 A | * | 9/1961 | MacNeary | 312/235.3 |
| 3,550,448 A | * | 12/1970 | Ensign | 374/141 |
| 4,073,240 A | * | 2/1978 | Fly | 108/20 |
| 4,372,631 A | | 2/1983 | Leon | |
| 4,500,150 A | * | 2/1985 | Leibensperger et al. | 439/502 |
| 5,366,208 A | | 11/1994 | Benjamin | |
| 5,673,687 A | * | 10/1997 | Dobson et al. | 128/204.14 |
| 5,826,286 A | | 10/1998 | Cranston | |
| 5,938,185 A | | 8/1999 | Kletter | |
| 6,036,011 A | * | 3/2000 | DeCurtis et al. | 206/320 |
| 6,240,856 B1 | | 6/2001 | Paskey et al. | |
| 6,386,531 B1 | | 5/2002 | Prosser | |
| 6,536,358 B1 | * | 3/2003 | Fears | 108/116 |
| 6,561,107 B1 | | 5/2003 | Wood et al. | |
| 6,588,863 B1 | | 7/2003 | Yatchak et al. | |
| 6,595,144 B1 | | 7/2003 | Doyle | |
| 6,651,970 B2 | | 11/2003 | Scott | |
| 6,749,207 B2 | | 6/2004 | Nadeau | |
| 6,776,105 B2 | * | 8/2004 | Rivera et al. | 108/34 |
| 7,009,840 B2 | | 3/2006 | Clark et al. | |
| 7,946,253 B2 | * | 5/2011 | Smith et al. | 119/756 |
| 2005/0188902 A1 | | 9/2005 | Savoie | |
| 2008/0072802 A1 | * | 3/2008 | de Oliveira | 108/12 |
| 2008/0127417 A1 | | 6/2008 | Harty | |
| 2009/0146353 A1 | | 6/2009 | Hashim | |

FOREIGN PATENT DOCUMENTS

GB 689617 A 4/1953

* cited by examiner

*Primary Examiner* — Janet M Wilkens

(74) *Attorney, Agent, or Firm* — Schnader Harrison Segal & Lewis LLP

(57) ABSTRACT

A system for an adjustable, portable stand for supporting a portable, non-surgical medical device such as a CPAP or BiPAP machine. The system includes an adjustable and portable stand and a carrying case. The stand includes a platform with a recess along the periphery of the top surface, and a central portion to support the medical device. The recess includes at least one hole for fluid released from the medical device to flow from the central portion of the platform to the recess, through the hole, to a tray beneath the platform. The tray is slidably engaged to and beneath the platform. The platform is supported by a plurality of members releasably attached to one another, and is adjustable in height.

16 Claims, 11 Drawing Sheets

MEDICAL DEVICE STAND AND SYSTEM

This application is based on, and claims priority to, U.S. provisional application Ser. No. 61/250,360, filed Oct. 9, 2009, and entitled Adjustable Portable Stand with Water Safety Tray for CPAP and BiPAP Machines.

BACKGROUND

The invention relates to a stand to support and to collect fluid discharged or released by a medical or therapeutic device such as a continuous positive airway pressure (CPAP) machine, or a bi-level positive airway pressure (BiPAP) machine (thereafter collectively as CPAP machines). The CPAP machine is commonly employed to treat sleep apnea.

CPAP therapy provides a constant airflow which holds the airway open so that uninterrupted breathing is maintained during sleep. The CPAP machine consists of a flexible tube connecting a filtered air pump to a mask or other interface devices worn over the nose or mouth. The mask is worn at night or any time a user goes to sleep. The machine creates a constant-pressured forced airflow which pushes air through a user's airway passage at a pressure high enough to prevent apneas.

People are often discouraged from using CPAP machines due to discomfort and side effects, such as sneezing, nasal discharge and dryness, dryness in throat and mouth, sore tongue, and nosebleeds. Nasal or upper airway dryness is a side effect of unhumidified CPAP use and is a common reason people terminate an otherwise beneficial therapy. Heated humidification is found to improve both compliance and comfort. Manufacturers of CPAP machines often incorporate heaters and humidifiers to the CPAP machines to add heated vapor in the forced airflow to reduce dryness. However, the humidifiers can produce condensation in the tubing, which causes water to leak from the connection between the hose and the machine. Water may also leak from the reservoirs or chamber of the built-in humidifier in a CPAP machine. This can cause damage to furniture, flooring, or other items with which the water comes in contact. Additionally, since the machine is electrified and runs overnight, often by the side of the user's bed, water leakage may lead to electrocution, or cause the electrical wiring to short and create a fire hazard. Accordingly, the inventor sets out to develop a system that reduces or eliminates water leakage problems.

Doctors often recommend placing the CPAP machine at the same height as the top of the mattress on a bed stand rather than on the floor because air drawn from the floor or under the bed tends to be cooler, which creates discomfort to users. CPAP machine users may not have an appropriate height nightstand or other structure. This may be a particular problem when travelling. Accordingly, the inventor also sets out to develop a system that includes an adjustable and portable stand that allows a user to use the machine at a proper height, regardless of the available furniture or support structures.

SUMMARY OF THE INVENTION

A system for supporting a portable, non-surgical medical device such as a CPAP or BiPAP machine is presented. An illustrative embodiment of the system includes an adjustable and portable stand and a carrying case. The stand includes a platform with a top surface to support the medical device, a receptacle slidably engaged to and beneath the platform to collect fluids and a plurality of members to support the platform and the fluid-collecting receptacle. The platform has at least one opening on the top surface. The central portion of the substantially level top surface to support the medical device. A securing component may be employed to hold the medical machine in the center portion of the platform. In a particular embodiment, the platform, a recess along the periphery of the platform, wherein the opening(s) extend through the floor of the recess so fluid from the medical device flows from the central portion of the platform to the recess, then through the hole, to the receptacle beneath the platform. The watertight receptacle is slidably engaged with and beneath the platform so it may be removed and emptied. An overflow sensor can be attached to the system to detect excessive fluid from accumulating on the top surface of the platform or in the receptacle. The modular leg members connectable to the platform are releasably attached to one another for easy disassembly and are adjustable in height.

In an exemplary embodiment of the invention, the disassembled modular leg members and optional accessories fit into the watertight receptacle for storage and transport. The platform can serve as a lid to the slidably engaged receptacle, and can be further secured by a fastening device. The receptacle and lid can be configured as a carrying case or can be stored in a separate case.

The adjustable, portable stand is preferably made of electrically non-conductive material such as wood, plastic, or glass. Alternatively it can be made of metal with an electrically non-conductive coating.

In another embodiment, the center portion on the top surface of the platform is raised above the edge of the platform. The center of the raised portion remains flat, and securely holds the medical device in place. The raised portion gradually slopes downward such that fluid leaked from the medical device runs to the recess through one or more holes into the collecting receptacle. The medical device remains dry at all time. The optional securing component includes brackets to secure the medical device on the raised platform surface. The securing component may be adjustable, and is positioned approximately in the center portion of the raised platform. One or more waterproofed ground fault circuit interrupter (GFCI) electrical outlets can be wired into the platform as an extension for the user to plug in the medical device. An electrical cord management component is optionally positioned on the side of the platform to ensure that the electrical cord does not entangle with any of the medical device components or to secure the cord in a manner reducing the likelihood of accidents.

DETAILED DESCRIPTION OF THE INVENTION

Figure 1:
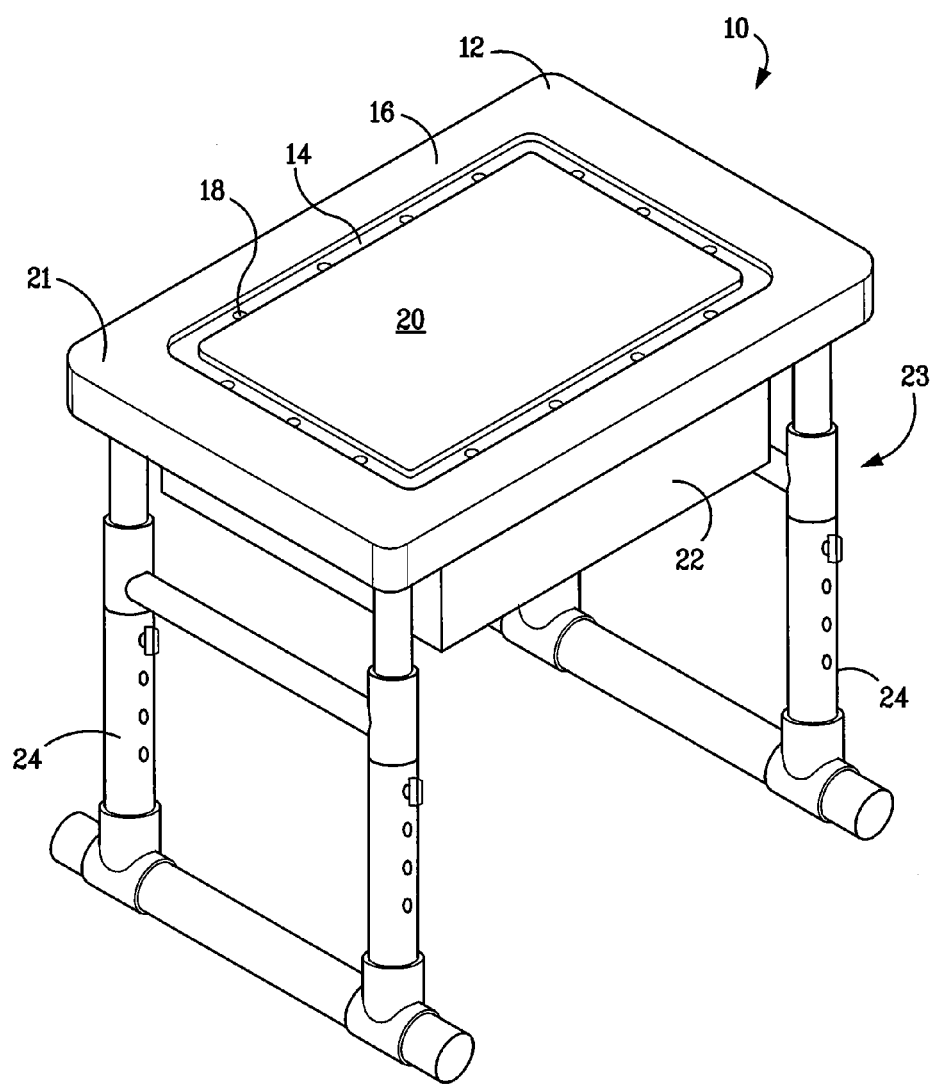
FIG. 1 is an isometric view of the stand according to an illustrative embodiment of the invention.

As shown in the various figures, a portable and adjustable stand for supporting a non-surgical medical device is presented. The stand is used to control fluid leakage from the medical device. The stand includes a platform, a receptacle beneath the platform and a plurality of adjustable and releasably connected members as legs to the platform. This specification is written with particularity to portable, non-surgical medical device which is a CPAP or BiPAP machine, with or without built-in humidifiers, but is not limited to that application. The entirety of this disclosure is applicable even where the equipment is other than a CPAP or BiPAP machine.

CPAP machines are portable, low-pressure air generators connected by tubing to a nasal or full-face mask to be worn during sleeping. The CPAP mask uses air pressure to push the tongue forward and open the throat and airway. The increased pressure created by the CPAP machine makes it easier for air to flow into the lungs. The CPAP mask should have a seal around the mouth and/or nose to avoid air leakage. Elongated tubing connects the mask to the CPAP machine. The generated airflow of the CPAP machine may be relatively colder than the user's body temperature. The difference in temperature creates condensation, which may gather inside the elongated tubing, and flow to the connection point between the CPAP machine and the tubing. Fluid such as water may leak out of the machine or may flood the internal components of the machine. This can cause damage to surrounding objects. Additionally, electrocution of the user or fire from short circuit inside the machine may occur. Manufacturers recommend placing the machine at a specific height, usually at the same height as the top of the mattress to avoid accumulation of condensation. In addition, many users complain of dryness in the forced airflow at the mask. Some models of CPAP machines incorporate cooled or heated humidifiers to moisten the air to be delivered to the mask. Users have also reported leakage from the humidifier reservoir or water chamber.

Since the CPAP machine operates throughout a user's sleep cycle, and is placed near the user during its operation, such as on the floor or at a bed stand near the user, electrocution or fire hazard is a serious threat. Water leaked from the CPAP machine should be isolated and removed immediately away from the machine to reduce such risks.

As part of the therapy to treat obstructive sleep apnea, doctors recommend using the CPAP machine every night, including during travel. When a user is away from home, it is often difficult to position the machine at the recommended height to avoid accumulation of condensation in the tubing. Accordingly, a portable, adjustable stand as described below accommodates the CPAP machine at a selected height for the machine to function properly. In addition, the portable, adjustable stand has a recess on the top surface and a receptacle beneath to collect discharged or leaked fluid from the machine. One or more holes within the recess floor allow the collected fluid to be directed to a receptacle. The stand comprises modular components that can be disassembled and stowed in a compact and portable fashion for ease of traveling and storage.

Figure 3:
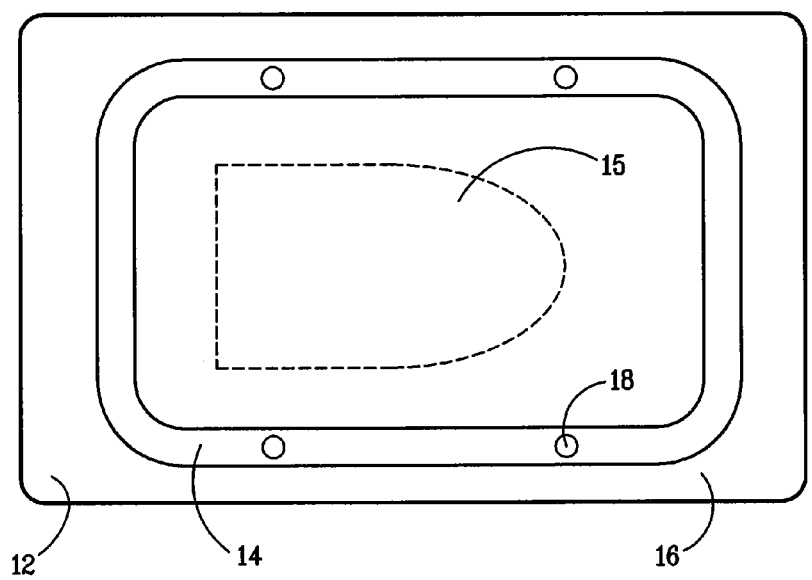
FIG. 3 is a plan view of the top surface of the platform with a CPAP machine positioned on top according to an illustrative embodiment of the invention.

FIG. 1 is an isometric view of the adjustable, portable stand 10 according to an illustrative embodiment of the invention. It includes a platform 12, a receptacle 22 and a support system 23 that includes a plurality of members 24 supporting the platform 12 and receptacle 22. According to an illustrative embodiment, the platform 12 is substantially flat and rectangular. The shape of the platform is not limited to rectangular, and can be any shape, including oval or circular. The top surface 16 of the platform 12 is substantially level and includes at least one recess 14 extending, for example along the periphery of the surface. The recess 14 divides the top surface 16 into two regions: a central portion 20 defined within the inside boundary of the recess 14 and a peripheral portion 21 extending from the outside edge of the recess to the edge of the platform. A non-surgical medical device 15 such as a CPAP machine can rest at the central portion 20 of the platform 22 as shown in FIG. 3.

Figure 2:
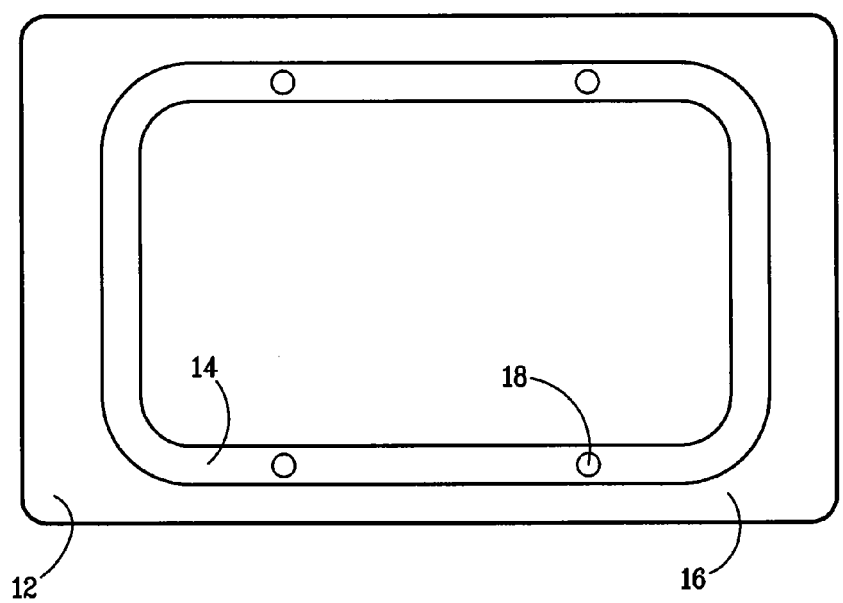
FIG. 2 is a plan view of the top surface of the platform according to an illustrative embodiment of the invention.

FIG. 2 is a plan view of the top surface 16 of the platform 12 according to an illustrative embodiment of the invention. The recess 14 extends along the periphery of the top surface 16 of the platform 12, and includes at least one hole 18 defined in the recess 14. The holes 18 and the recess 14 are in fluid communication with the central portion 20 of the platform such that any fluids run off from the CPAP machine will flow into the recess 14 to separate the machine from moisture to prevent electrical short circuit or accidental electrocution of the user, and to control fluid to reduce or eliminate damage to surrounding objects. One or more recesses 14 may be defined on the top surface 16, and are not limited to be positioned at the periphery of the platform 20. In the illustrative embodiment as shown in FIG. 2, four holes are defined in the recess 14 for drainage. One or more holes 18 can be defined within the recess 14 and in the central portion 20 of the platform 12. An illustrative recess depth range is about ¼ inch to about ½ inch, and an illustrative recess position is within about ¼ inch to about 1 inch from the edge of the platform. In an illustrative embodiment of the invention, the platform has an area in the range of about $10 \times 18$ in$^2$ to about $16 \times 24$ in$^2$.

In a further embodiment of the invention, the platform has a plurality of openings or holes, rather than a recess with holes. Provided that the receptacle extends beyond the holes and the holes are positioned in the platform so as to allow all fluid released from the medical device to pass therethrough, the stand should operate in a similar manner to the previously described and pictured embodiments.

Figure 4:
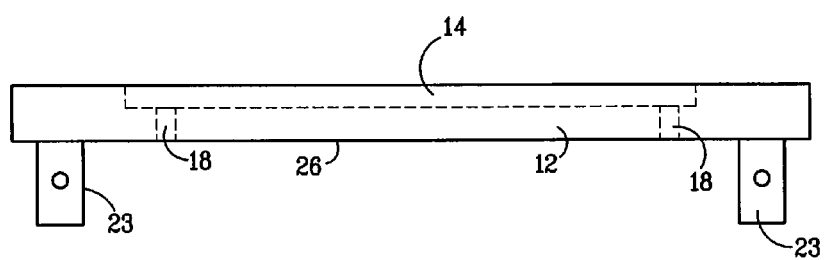
FIG. 4 is a side view of the platform according to an illustrative embodiment of the invention.
Figure 5:
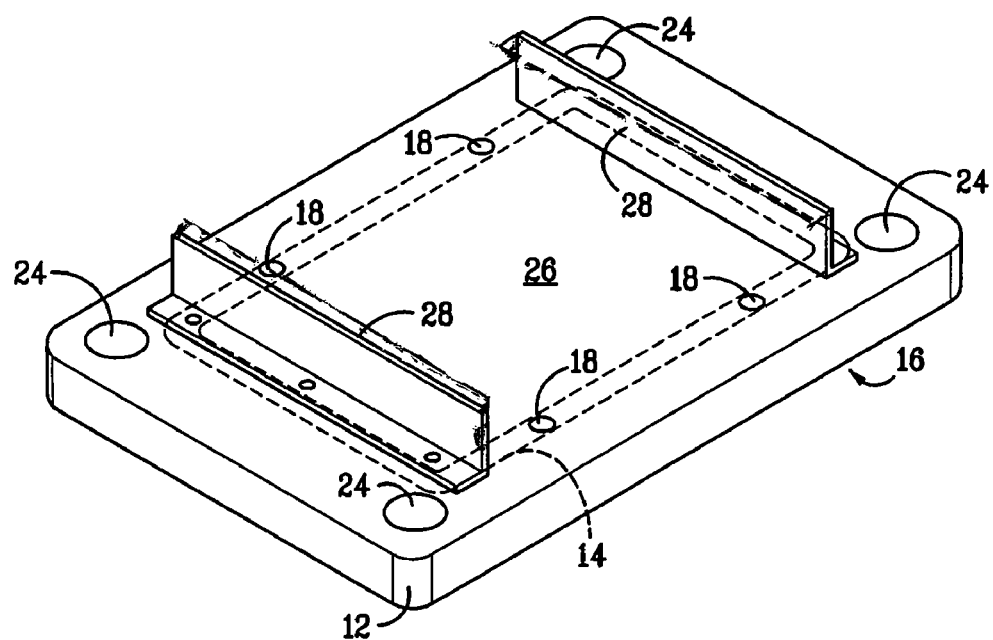
FIG. 5 is a plan view of the bottom surface of the platform according to an illustrative embodiment of the invention.

FIG. 4 depicts a side view of the platform 12 and a portion of the members 24 of the collapsible support system 23. The holes 18 extend from the recess 14 through the bottom surface 26 of the platform 12. FIG. 5 shows a plan view of the bottom surface 26 of the platform 12. It includes slots 28 for the receptacle 22 to be slidably engaged to the platform. Other forms of detachable engagement of the receptacle and platform are also within the scope of the invention. Holes 18 extend from the recess 14 and top surface 16 to the bottom surface 26. Some members 24 of the support system 23 are also attached to the platform. As depicted in FIG. 1, the receptacle 22, which can be in the form of a tray or drawer is positioned beneath the platform to collect fluid leaked from the CPAP machine. Fluid flows from the central portion 20 of the platform 12 to the recess 14, then through the holes 18 to be collected in the receptacle 22. An overflow sensor may be optionally included in the receptacle to detect any overflow in the receptacle at pre-determined levels to prevent leakage to a nightstand or the floor for example. The user may remove the receptacle 22 by sliding it out from beneath the platform 12, or otherwise detaching it, to empty the collected fluid.

The empty receptacle may also be used to store the members of the support system 23 when the stand is disassembled. In an illustrative embodiment of the invention, the components of the stand and the receptacle are dimensioned so the disassembled members 24 of the support system 23 can be stored in the receptacle. The dimensions of the receptacle can be further provided to accommodate the medical device and various accessories.

The receptacle 22 is made of a water-resistant material, but is not limited to this type of material. A water-resistant liner can also be placed in the receptacle 22 to collect the leaked fluid. The liner can be made of a variety of material including but not limited to plastic.

Figure 6:
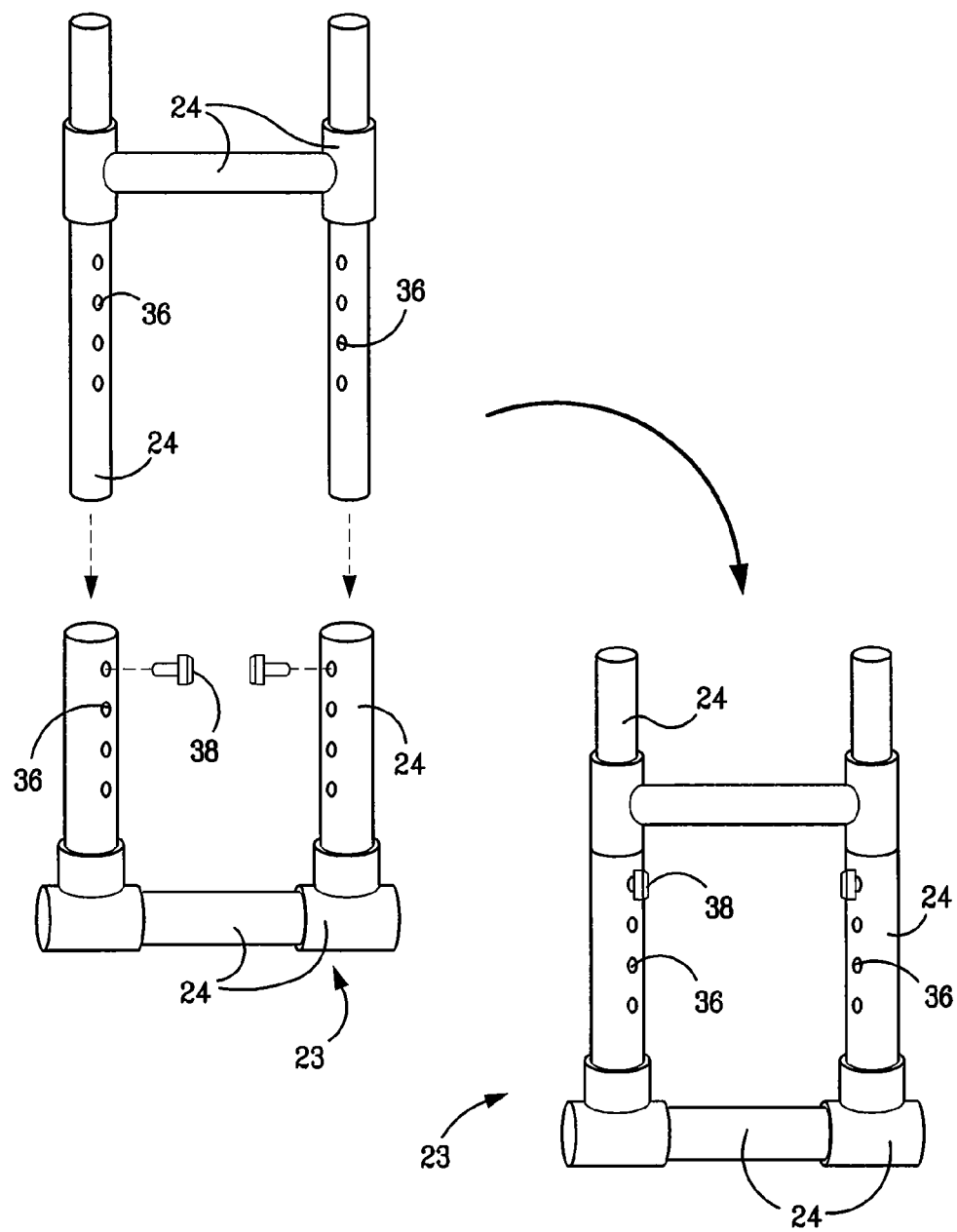
FIG. 6 is a plan view of the releasable support members according to an illustrative embodiment of the invention.

FIG. 6 depicts members 24 of the collapsible support system 23 in a disassembled configuration. As shown in FIG. 1, members 24 of a support system 23 are attached to the horizontal platform 12 as legs to provide structural support and stability to a stand 10. The members 24 are modular and are releasably connected to the platform 12 and to each other. The modular members 24 preferably can be connected without the use of tools. In this embodiment, one or more telescopically adjustable legs are securable in a plurality of heights. The legs have a plurality of apertures 36 positioned longitudinally along each telescoping section of the legs such that the apertures from one telescoping section can be aligned with apertures from another telescoping section. The stand can further include one or more fastening devices 38 insertable through the aligned leg section apertures to secure the legs at a height selectable from the plurality of heights. The fastening device includes but is not limited to a set of screws, bolts or pins. Horizontal members 38 are optionally connected between pairs of legs to provide additional stability to the stand 10. The legs can be made from a variety of materials including but not limited to plastic.

Figure 7:
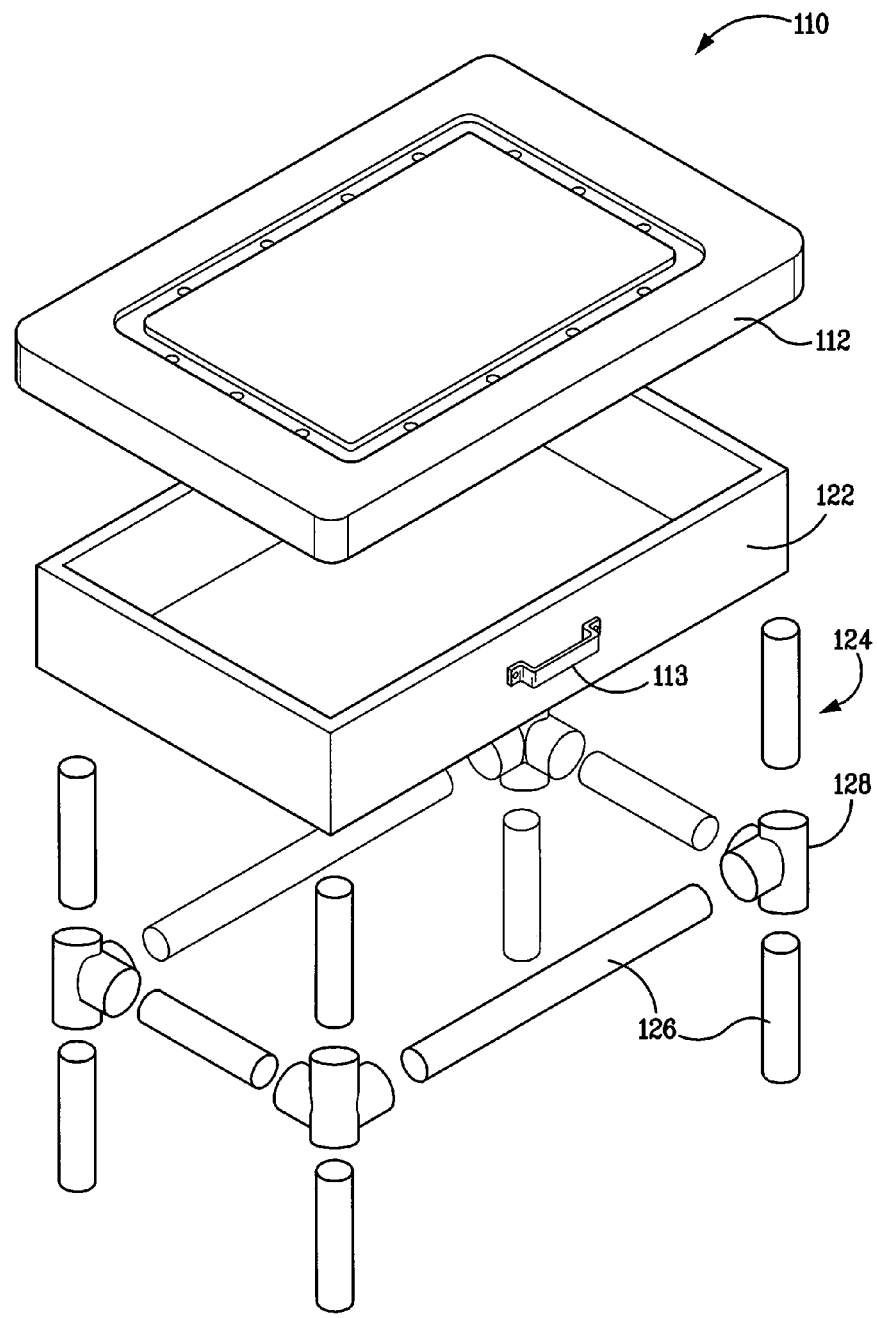
FIG. 7 is an exploded view of the stand according to an illustrative embodiment of the invention.
Figure 8:
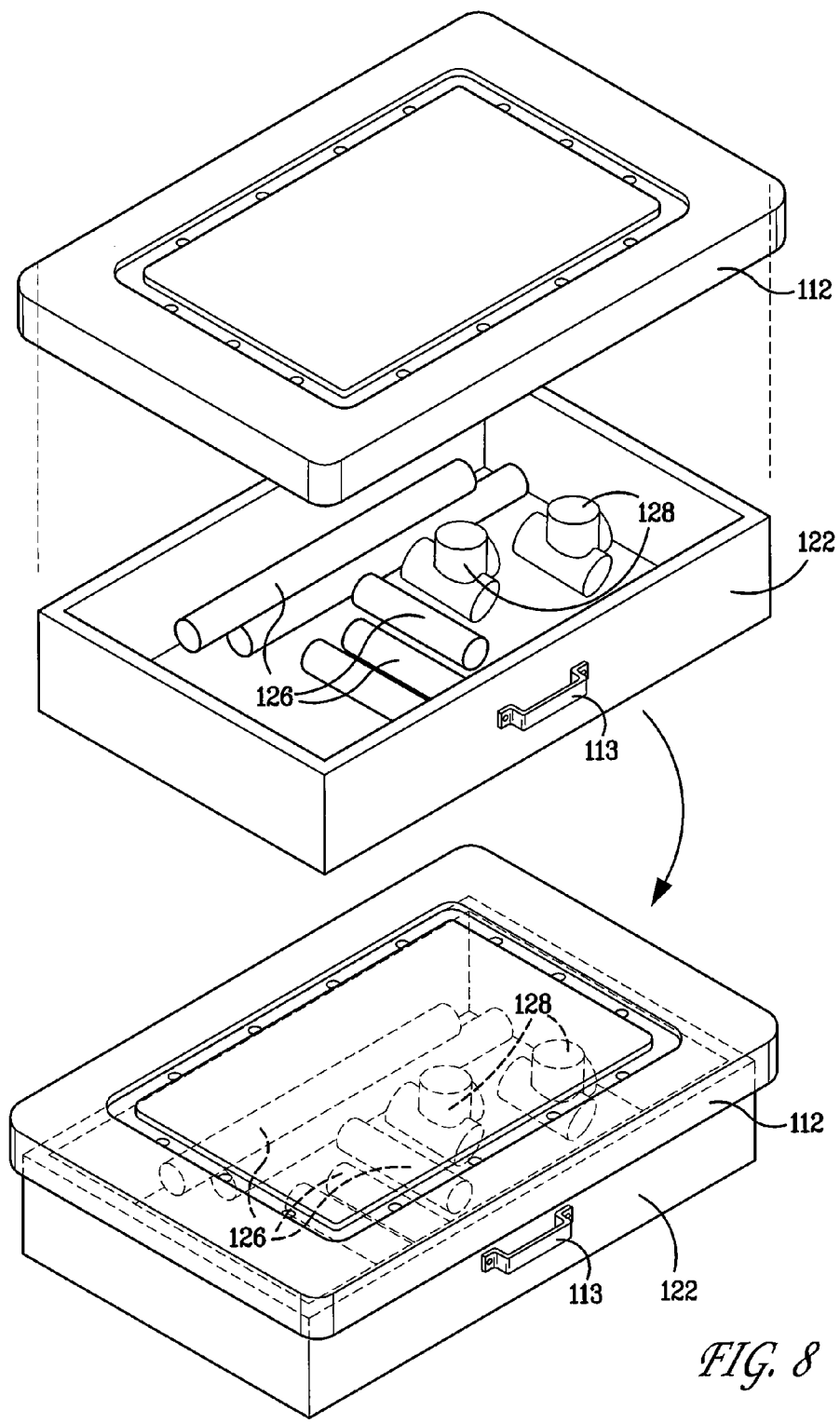
FIG. 8 is an isometric view of the disassembled portable, adjustable stand of FIG. 7.

FIGS. 7 and 8 show the exploded isometric views of another illustrative embodiment of the portable, adjustable stand. The stand 110 includes a platform 112, a receptacle 122 releasably engaged to the platform 112 and a support system 124 connected to the platform 112. The receptacle 122 and the platform 112 slidably engaged with one another can serve as a container for other stand components and possibly the medical device and accessories. An optional handle 113 allows a user to easily slide the receptacle from the platform to be emptied. It also works as the handle to the receptacle, if used as part of a carrying case as illustrated in FIG. 8. The adjustable support system 124 includes a plurality of modular and releasably connected members. In the embodiment shown in FIG. 7, the adjustable support system 124 is formed by connecting a plurality of linear members 126 with connectors 128 that are releasably connected to one another. The support system is then connected to the platform either directly or indirectly. In this illustrative embodiment, the modular members 126 are straight, and the connectors 128 are set in right angle. In assembly, they form a rectangular support system. However, the shape of the modular members and connectors are not limited to straight and right angled, and may be curved or in combination thereof to form support systems of different shapes and configurations.

Upon disassembly of the adjustable support system 124, the modular members 126 and connectors 128, along with various accessories provided below can be stowed in the receptacle as illustrated in FIG. 8. A locking device is optionally attached to the carrying case to secure the platform 112 to the receptacle 122 to ensure that the stowed members 126, connectors 128 and other contents in the receptacle remain in place.

Figure 9:
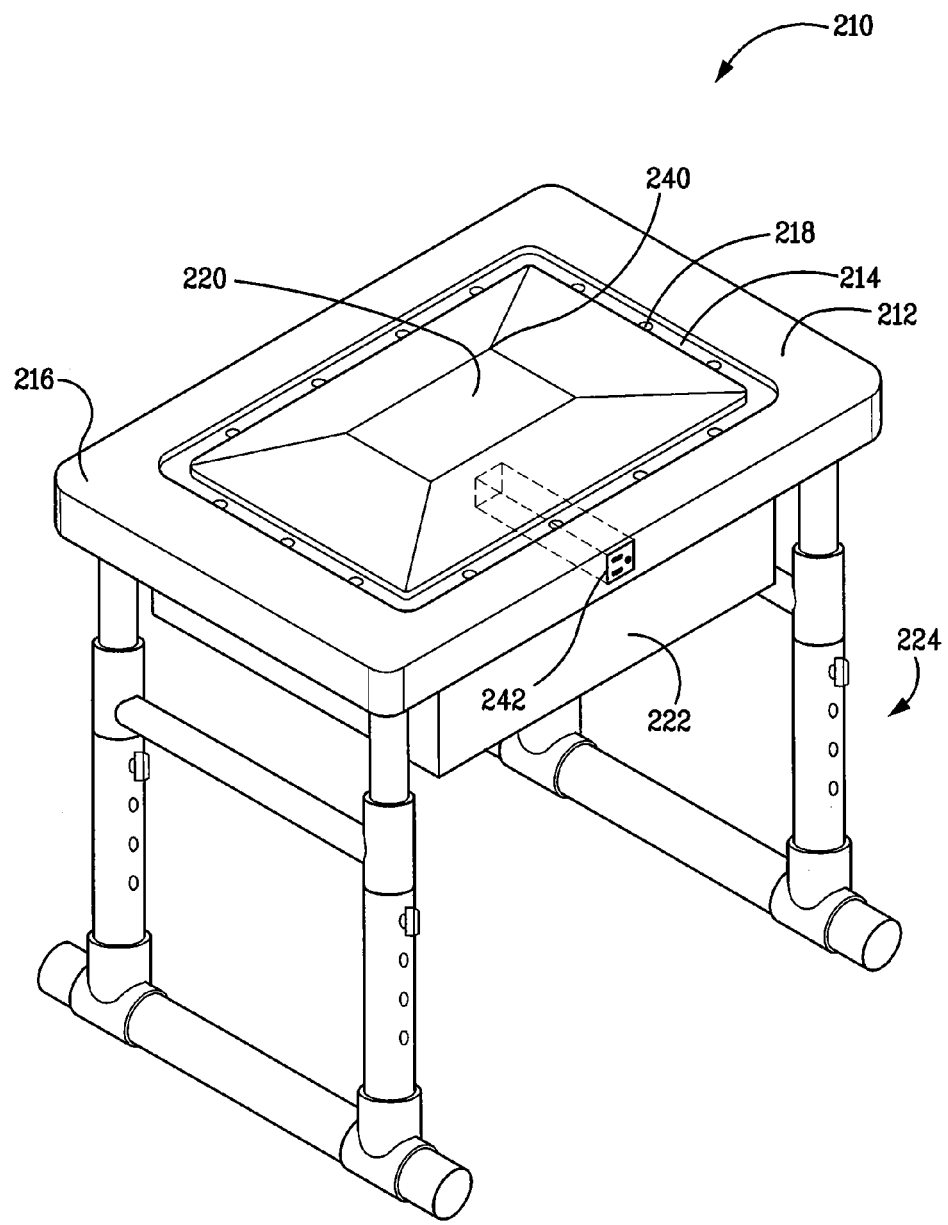
FIG. 9 is an isometric view of the stand with a raised central portion of the platform according to an alternative embodiment of the invention.
Figure 10:
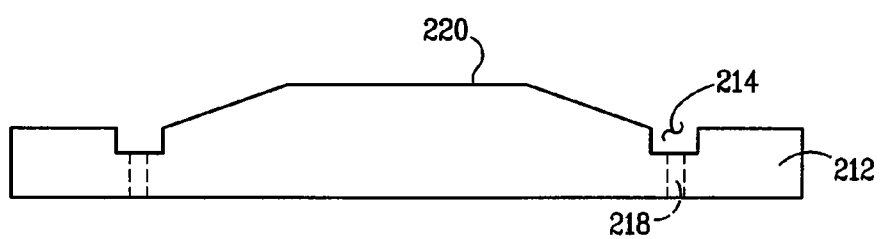
FIG. 10 is a side view of the platform of FIG. 9.

FIGS. 9 and 10 show the isometric and side views of another illustrative embodiment of the portable, adjustable stand. The stand 210 includes a platform 212, a receptacle 222 slidably engaged to the platform 212 and a support system 224 connected to the platform 212. One or more recesses 214 extend along the entire periphery of the top surface of the platform 212, and divide the platform into two general portions, a raised central portion 220 defined within the inner boundary of the recess 214, and a peripheral portion 216 extending from the outside edge of the recess 214 to the edge of the platform. The raised central portion 220 is substantially flat to receive a CPAP machine resting on top. The raised central portion 220 is at a height above the peripheral portion 216 and the recess 214 as shown in the side view in FIG. 10. The raised portion 220 gradually slopes downward to allow fluid to flow from the CPAP machine into the recess 214. One or more holes 218 are in the recess 214 for drainage to the receptacle 222.

One or more ground fault circuit interrupt (GFCI) outlets 242 are built into the platform 212 to provide electrical outlets to plug in the CPAP machine. The GFCI outlet protects a person from electrical shock by interrupting a household circuit when there is a difference in the currents in the hot and neutral wires. The difference in current indicates an abnormality in the current flow. If the CPAP machine is not properly grounded, the leaked fluid, which is conductive, creates an electrical path for current to flow from the hot wire inside the CPAP machine through the user to ground. As a result, the user will be electrocuted, which could be fatal. The GFCI can sense difference in the currents when the current in the hot wire is diverted through the user to ground. As soon as the GFCI senses that, it trips the circuit and cuts off the electricity, and prevents electrocution of the user.

The platform can be made of a variety of material including electrically non-conductive material such as wood, plastic and glass. Metal may also be used as long as an electrically non-conductive coating is applied to the surface to prevent electrocution.

A securing component 240 such as but not limited to one or more anchors, raised edges or brackets may be incorporated in the central portion to secure the CPAP machine to provide additional stability to the machine.

An electrical cord management component or an electrical cord keeper (not shown in the figures) can be incorporated into the system to keep the cord from entangling with the tubing connected to the CPAP machine, and to keep the cord away from the leaked fluid.

Figure 11:
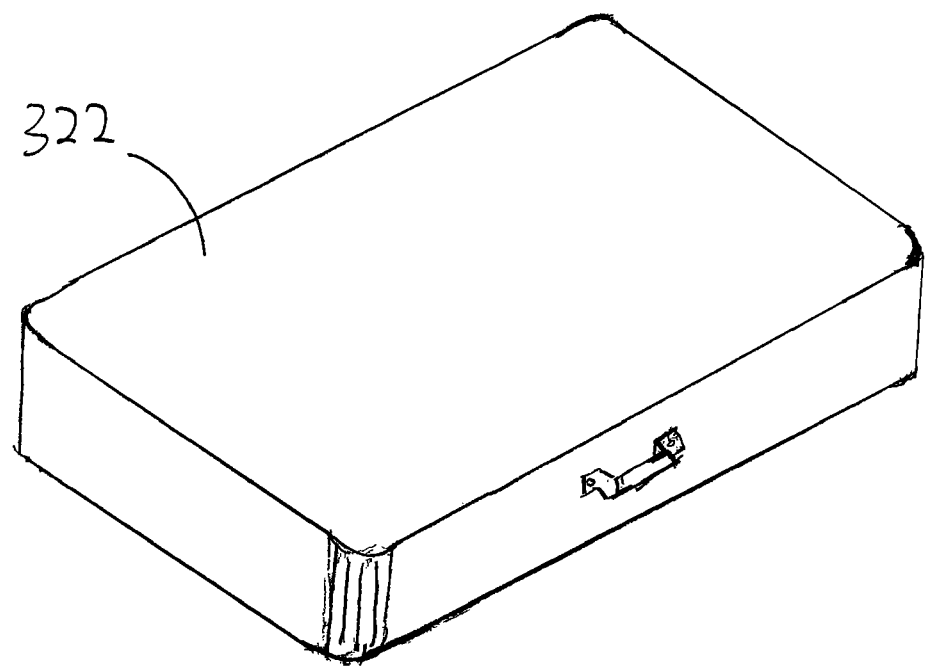
FIG. 11 is an isometric view of the carrying case according to an illustrative embodiment of the invention

According to the illustrative embodiment shown in FIG. 11, the stand may be disassembled into parts, and be stored in a carrying case for the CPAP user to take on the road. The system, including the stand and the carrying case, can be carried on an airplane or in other travel situations.

It should be readily recognized that the shape of the platform and the shape of the raised central portion are irrelevant so long as they do not impede the flow of fluid leaked from the CPAP machine to the recess. Contemplated shapes include simple geometric shapes, rectangles, circles, oval, or more complex combinations of shapes. The position of the holes on the platform is not limited to be in the recess, and may be generally placed within the central portion on the platform. Regardless, the recess and platform provides ample surface area for fluid to be drained away from the CPAP machine to avoid accident of electrocution or short circuit sparks creating a fire.

Similarly, it should also be readily recognized that the configuration and cross-sectional shape of the members of the support system are irrelevant so long as they provide stability and structural support for the platform and receptacle to separate leaked fluid from the CPAP machine. Contemplated shapes for the cross section areas of the members include simple geometric shapes, circle, oval, square, rectangles, or more complex combinations of shapes. The members of the support system are also not limited to be configured as four legs supported by horizontal connecting members. Regardless, the support system provides support to the platform to raise it to a height recommended by the doctors or manufacturers of the CPAP machines.

Various features of the embodiments described herein and their equivalents can be combined or substituted to form other embodiments of the invention.

Other modifications and embodiments of the preferred embodiments discussed above can be made, and are considered within the scope of invention. The above disclosure is meant to include non-limiting examples of the invention.

The invention claimed is:

1. A system to accommodate a medical device comprising:
   a stand configured to support a positive airway pressure machine;
   wherein the stand is adjustable in height with respect to the user for proper functioning of the positive airway pressure machine the stand including:
   a platform having a top surface with a substantially level top portion to support the medical device and a bottom surface opposed to the top surface;
   the top surface having a recess to receive fluid released by the medical device, the recess having a plurality of openings extending through a bottom surface of the recess, and wherein the recess divides the top surface into a first central surface region and a second peripheral surface region;
   a receptacle releasably engaged with and beneath the platform to collect fluid discharged from the medical device and directed to the receptacle through the plurality of opening wherein the plurality of openings are positioned above an opening of said receptacle; and
   a collapsible support system comprising a plurality of modular members connectable to the platform, wherein at least some members are releasably connected to one another, and wherein the collapsible support system is adjustable in height.

2. The system in claim 1 further comprising a securing component to adaptably receive and secure the medical device to the stand.

3. The system of claim 1 further comprising a carrying case configured to carry the platform, the receptacle, and the support system.

4. The system of claim 3 wherein the carrying case is further configured to carry the medical device.

5. The system of claim 1 wherein the recess extends around the entire periphery of the platform.

6. The system of claim 1 wherein the receptacle is dimensioned to hold the modular members.

7. The system of claim 6 wherein the platform is configured to be a lid to the receptacle.

8. The system of claim 1 wherein the recess is positioned within about ¼ inch to about 1 inch from the edge of the platform.

9. The system of claim 1 wherein the support system comprises:
   at least four telescopically adjustable legs securable in a plurality of heights.

10. The system of claim 9 wherein the legs comprise a plurality of apertures positioned longitudinally along each telescoping section of the legs such that the apertures from one telescoping section can be aligned with apertures from another telescoping section, the stand further comprising components insertable through the aligned leg section apertures to secure the legs at a height selectable from the plurality of heights.

11. The system in claim 1 wherein the platform is configured to support a humidifier, a continuous positive airway pressure (CPAP) machine or a bi-level positive airway pressure machine.

12. The system of claim 1 wherein the platform has an electrically non-conductive coating.

13. The system of claim 1 wherein the platform and members are made from a non-conductive material.

14. The system of claim 1 wherein the receptacle is slidably engaged with the platform.

15. The system of claim 1 wherein the modular members of the collapsible support system can be connected without the use of tools.

16. A system for use with a portable medical device comprising:
   an adjustable, portable stand comprising:
      a platform having a top surface and a bottom surface;
      the top surface having a recess extending along an entire periphery of the top surface, wherein the recess divides the top surface into a first central surface region and a second peripheral surface region;
      a plurality of hole through the recess extending through the platform bottom surface;
      a receptacle releasably engaged with and beneath the platform to collect fluid released by the medical device, collected within the recess, and directed to the receptacle through the plurality of hole, wherein the plurality of holes are positioned above an opening of said receptacle;
   wherein the platform is adjustably configured to accommodate a positive airway pressure machine; and
   a support system having one or more members detachably connected to the platform, wherein the members include legs that are adjustable in height; and
   a carrying case configured to carry the platform, the receptacle and the support system.

* * * * *